United States Patent [19]

Khuri-Yakub et al.

[11] Patent Number: 5,271,274
[45] Date of Patent: Dec. 21, 1993

[54] THIN FILM PROCESS MONITORING TECHNIQUES USING ACOUSTIC WAVES

[75] Inventors: B. T. Khuri-Yakub, Palo Alto; Sanjay Bhardwaj, Stanford; Krishna Saraswat, Cupertino, all of Calif.

[73] Assignee: The Board of Trustees of the Leland Stanford Junior University, Stanford, Calif.

[21] Appl. No.: 745,005

[22] Filed: Aug. 14, 1991

[51] Int. Cl.$^5$ .................... G01N 29/10; G01N 29/24
[52] U.S. Cl. .................................. 73/597; 73/627; 73/629; 73/643; 73/655; 73/657
[58] Field of Search ............... 73/597, 596, 598, 602, 73/620, 627, 628, 629, 643, 657, 655, 659, 661, 644

[56] References Cited

U.S. PATENT DOCUMENTS

| | | | |
|---|---|---|---|
| 4,253,326 | 3/1981 | Münnich et al. | 73/10 |
| 4,334,433 | 6/1982 | Takahashi et al. | 73/629 |
| 5,009,103 | 4/1991 | Sato et al. | 73/597 |
| 5,038,615 | 8/1991 | Trulson et al. | 73/597 |

FOREIGN PATENT DOCUMENTS

| | | | |
|---|---|---|---|
| 0305207 | 12/1988 | Japan | 73/596 |
| 0108908 | 4/1990 | Japan | 73/597 |
| 1200119 | 12/1985 | U.S.S.R. | 73/597 |
| 1221489 | 3/1986 | U.S.S.R. | 73/597 |
| 1516782 | 10/1989 | U.S.S.R. | 73/597 |
| 1619168 | 1/1991 | U.S.S.R. | 73/596 |

*Primary Examiner*—Hezron E. Williams
*Assistant Examiner*—Rose M. Finley
*Attorney, Agent, or Firm*—Flehr, Hohbach, Test, Albritton & Herbert

[57] ABSTRACT

A system and method is disclosed for measuring thickness of at least one film on a substrate by propagating an acoustic wave through the film on a substrate such that echo waves are generated and received by a transducer. An output signal is generated and processed to give a thickness value. The thickness valve is obtained from the time lapse between the propagated wave and receipt of the echo wave; by the frequency domain of the echo wave; or the phase of the echo wave.

17 Claims, 8 Drawing Sheets

FIG.—4

THIN FILM PROCESS MONITORING TECHNIQUES USING ACOUSTIC WAVES

FIELD OF THE INVENTION

This invention relates generally to a system and method for measuring film thickness.

BACKGROUND OF THE INVENTION

The process monitoring and control of the fabrication of VLSI circuits is critical for the achievement of high quality products. Traditionally, statistical process control (SPC) has been used as a means of identifying and solving fabrication problems. However, alternative methods are desirable because SPC is slow and expensive in that it requires of large amounts of empirical data gathering and analysis.

There are several commercially available instruments for measuring film thickness, each with limitations. For example, the ellipsometer which offers a noninvasive means for measuring film thickness is not useful for opaque films. The surface profilometer is useful for measuring opaque films, however, requires etching the film. The quartz crystal oscillator, which is capable of in-situ measurements of film thickness, only provides an indirect measurement of film thickness and furthermore cannot measure the film thickness at the point of interest, the wafer surface.

SUMMARY AND OBJECTS OF THE INVENTION

It is a general object of the present invention to provide a system and method for non-invasive, in-situ and real time film thickness measurements.

It is another object of the invention to use the propagation of an acoustic wave through a film and its reflection at a boundary to provide data for determining the film thickness.

It is yet another object of the invention to determine the time lapse between the propagation of the acoustic wave and the receipt of the reflected wave for calculating the film thickness.

It is a further object of the invention to determine the frequency domain response of the received reflected wave for calculating the film thickness.

It is yet a further object of the invention to determine the difference in the phase of the received reflected wave with respect to the propagated wave as data for calculating the film thickness.

It is another object of the invention to generate the acoustic wave by an ultrasonic transducer or a laser pulse.

The foregoing and other objects of the invention are achieved by a film thickness measuring system and method which includes means for propagating an acoustic wave through a film on a substrate, such film and substrate having a common boundary. The wave can be propagated by, for example, an ultrasonic transducer or a laser pulse. The propagated wave is at least in part reflected off the boundary. The reflected wave is received by a receiving transducer and an output signal is generated for processing.

There are at least three different types of signal processing disclosed herein. The first includes determining the time lapse between the propagation of the wave and the receipt of the reflected wave. The second includes determining the frequency domain of the reflected wave. The third includes determining the phase of the reflected wave. The thickness of the film therefore can be extrapolated.

DESCRIPTION OF THE PREFERRED EMBODIMENT

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications and equivalents, which may be included within the spirit and scope of the invention as defined by the claims.

Figure 1:
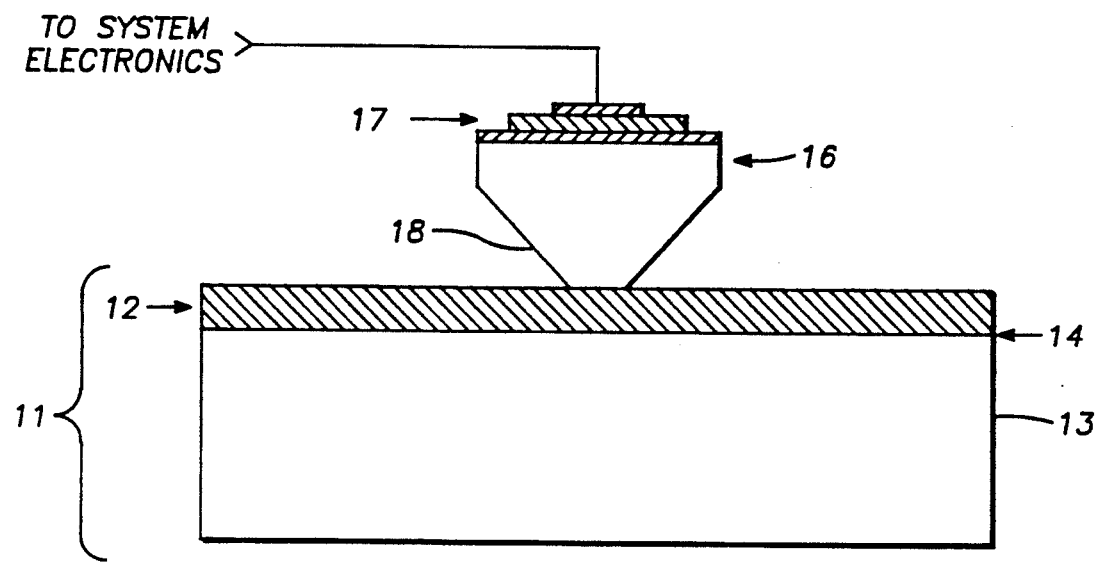
FIG. 1 schematically shows a film thickness measuring system in contact with the film side of a composite unit in accordance with the present invention.

Turning now to the drawings, wherein like components are designated by like reference numeral, attention is initially directed to FIG. 1. A composite unit 11 is composed of at least one film 12 on a substrate 13, having a common boundary 14. A film thickness measuring system 16 in which a short, longitudinal or transversal (shear) acoustic pulse is generated by a transducer 17 is also depicted therein. The transducer 17, a high-frequency ultrasound generator, in one embodiment is a zinc oxide (ZnO) piezoelectric thin film deposited on one end of a sapphire ($Al_2O_3$) or fused quartz buffer rod 18, operates in a frequency range of 1-7 GHz. The transducer 17 may be excited with, for example, a sharp edge or tone burst excitation. Furthermore, transducer 17 may also be a pulse laser or any other method of generating acoustic wave for propagation through the composite unit operating at a frequency conducive to the use of the present invention. Transducer 17, in the preferred embodiment also acts as a receiver to generate an output signal to the processing means, however, a different receiver may be provided.

The high-frequency ultrasound generator is coupled to the composite unit 11 by Hertzian contact. The contact end of the buffer rod 18 is polished with a radius of curvature on the order of a few centimeters wherein the weight of the device applies enough force to give a circular contact area of 100 μm in diameter. The thermal loading of the buffer rod is low because the contact area is small.

Figure 2:
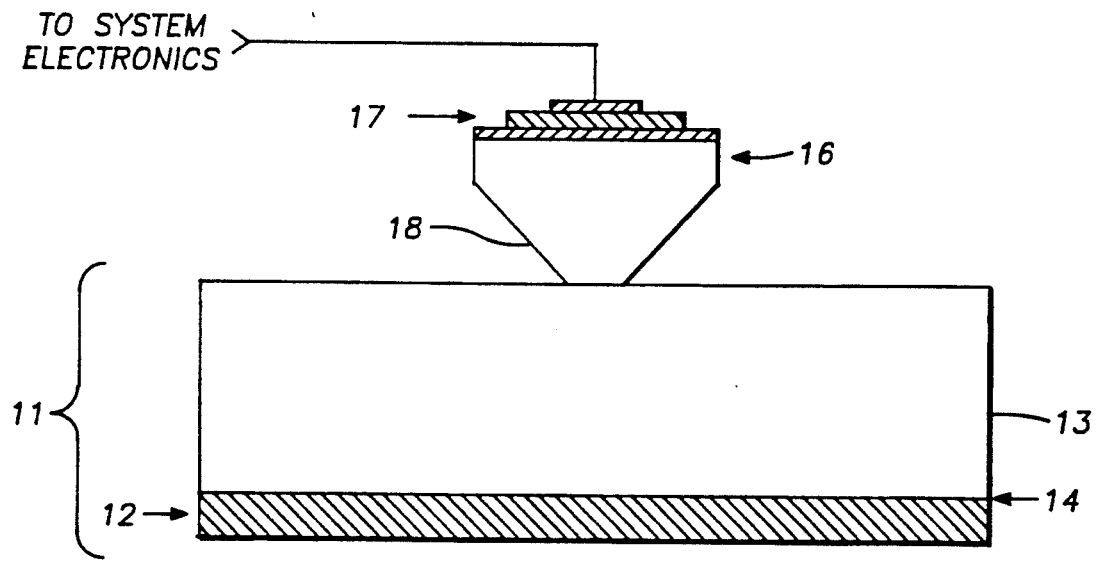
FIG. 2 schematically shows a film thickness measuring system in contact with the substrate side of a composite unit in accordance with the present invention.

FIG. 2 shows the buffer rod 18 making contact with the composite unit 11 from its back side. This configuration allows in-situ measurement, that is, measurements taken while the film is growing during deposition. Furthermore, it is possible to use transducer 17 as a receiver to monitor ultrasonic emission due to bombardment of the wafer by the deposited specie during deposition and infer the thickness of the film from a count of the emission events that took place during deposition. In-situ monitoring is particularly preferable in that less time is taken for the monitoring and measurement process during production of composite units than post process measurements.

Figure 3:
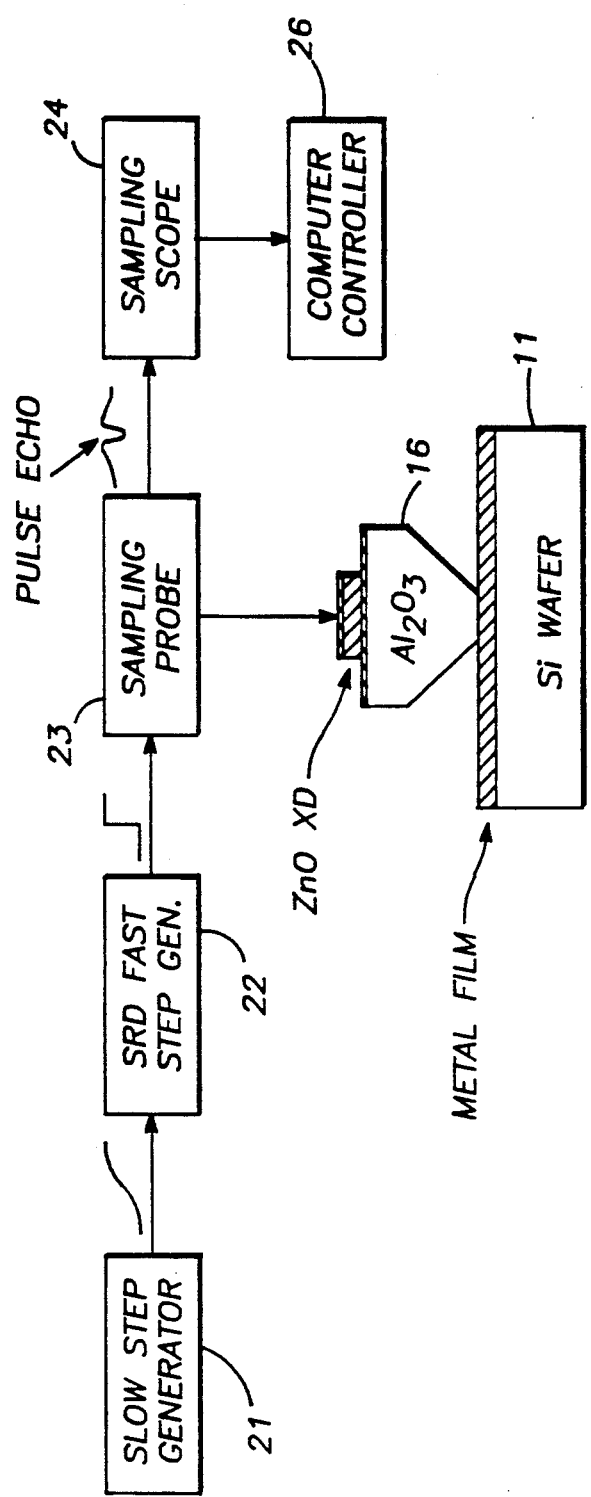
FIG. 3 is a schematic diagram of an electronic system for carrying out the present invention.

A generalized schematic of the system electronics is shown in FIG. 3 where the transducer 17 is excited with, for example, a slow step generator 21 and a step-recovery diode fast step generator 22. The signal propagated through the composite unit is reflected by the boundaries in the composite unit and between the composite unit and its environment. In a composite unit comprising only one film and a substrate, reflections occur at three boundaries, including that between the buffer rod 18 and the composite unit 11 surface, that between the film 12 and the substrate 13 and that between the composite unit 11 and air.

Figure 4:
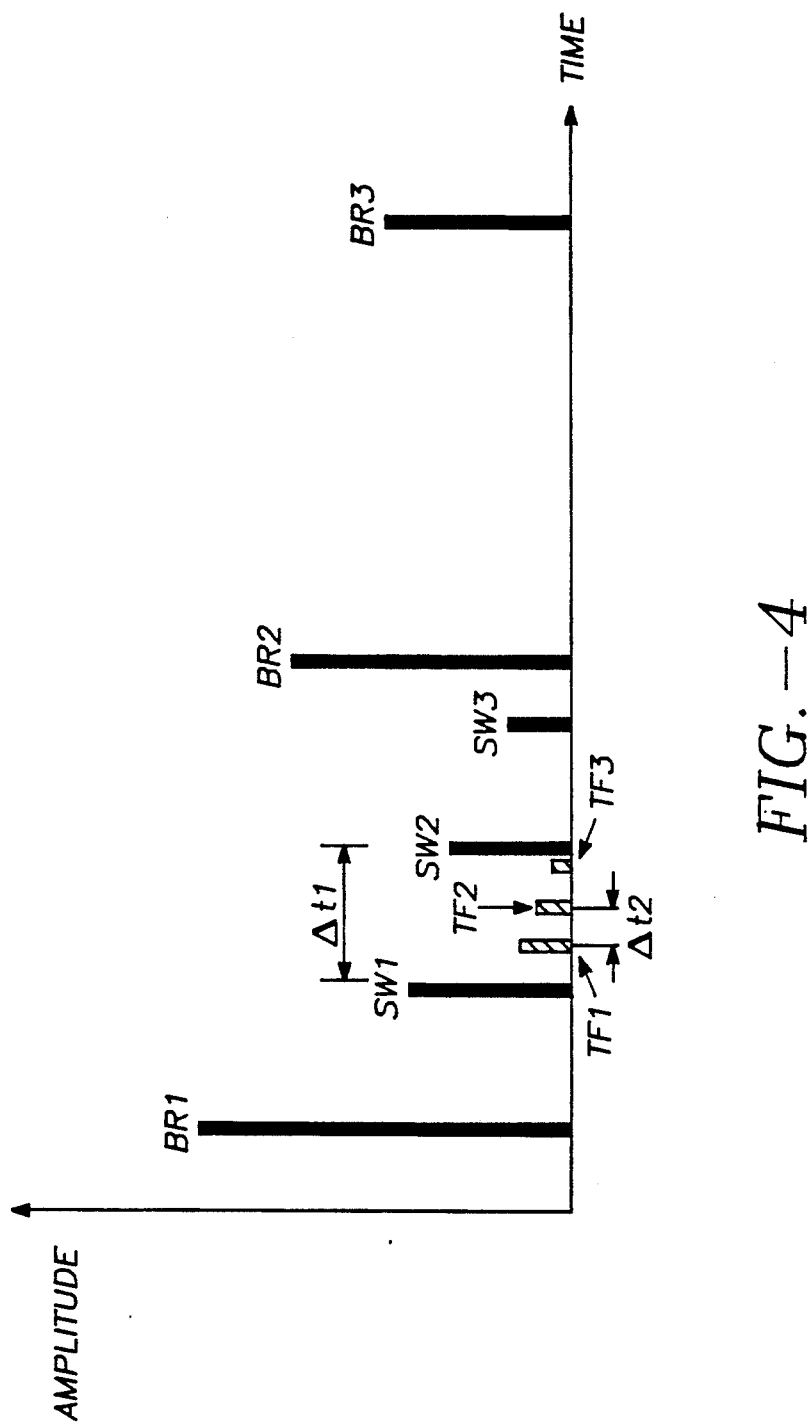
FIG. 4 graphically shows the amplitudes of reflections of an incident acoustic off boundaries in a system in accordance with the present invention.

Reflection of incident acoustic waves off boundaries of the composite unit and the TDR system are graphically shown in FIG. 4 wherein time is represented along the abscissa and the amplitude of reflected waves are represented along the ordinate. FIG. 4 shows that there are many reflected acoustic waves being sequentially propagated through the system as a result of the initially propagated wave, thereby causing an interference pattern. Therefore, it can be seen that analysis by, for example, Fourier analysis needs to be performed in order to separate the received interference pattern into its component parts.

The data gathered for FIG. 4 provides a direct measurement of attenuation in a film as a function of frequency. The thickness measurement is obtained by measuring temporally-separated reflections from the front and back sides of the film. Furthermore attenuation data may be obtained by fitting the experimental thickness data for the reflection coefficient as a function of frequency with theoretical data. Theoretical models can, for example, predict attenuation in materials as a function of the grain size.

As stated above, there are at least three different types of signal processing disclosed herein. The sampling probe 23 observes the reflected signals received by receiving transducer 17, and in the first instant, the time lapse between the propagation of the wave and the receipt of the reflected wave is determined. In the second instance, the frequency domain of the reflected wave is determined. In the third instance the phase of the reflected wave is determined.

Again referring to FIG. 3, a sampling probe 23 is shown which observes the reflected signals received by receiving transducer 17 and is communicated to the sampling scope 24 which stores and averages the measurement required for the calculation by computer controller 26. A film thickness of around 1.5 $\mu$m may be measured directly on the screen of a sampling oscilloscope by using the time domain as the form of measurement. A film thickness of around 0.15 $\mu$m is more readily measurable by using the frequency domain. The thickness of the film therefore can be extrapolated from the measurements of the sampling probe 23.

Figure 5:
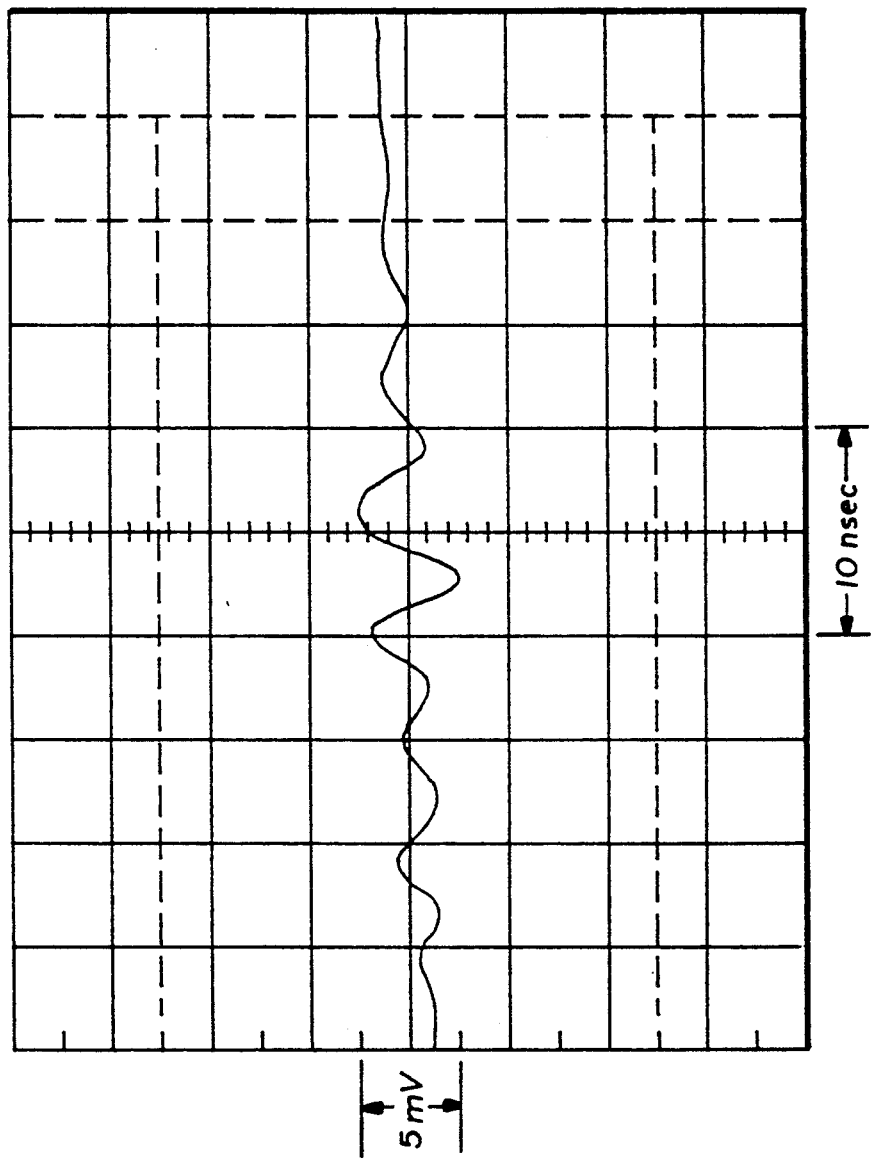
FIG. 5 graphically shows sample time domain data for reflected echoes.

In the instance where the time lapse between the propagation of a signal and the receipt of the reflected signal is determined, the thickness of the film is calculated by using the relation $X = \frac{1}{2}(V_0 \Delta t)$, where $V_0$ is the acoustic propagation velocity of the film. FIG. 5 graphically shows sample time domain data for reflected echoes from 2.1 $\mu$m gold film. The trace which was averaged 100 times provided an indication that the time separation between pulses was 1.3 nanoseconds.

In the acoustic time domain reflectometry (TDR) system, as stated above, the reflected signal r(t) from the acoustic system is sampled by the probe 23 and then is stored and averaged by sampling scope 24. In the preferred embodiment, the step-recovery diode electrical step is converted to an acoustic step by the ZnO transducer.

However, due to the transducer's finite bandwidth, a fast electrical step excites the step response s(t) of the ZnO transducer. Thus, the reflected signal r(t) as seen on the sampling scope 24 display is the convolution of the film response x(t) with s(t). To extract the film thickness information, the reflected signal r(t)=s(t) * x(t) is transformed into the frequency domain with a Fast Fourier Transform and is then filtered by $W(f) = S^*/(|S|^2 + N^2)$, where N is the system noise level. The Wiener filter removes the ZnO transducer's spectral response S(f) from the reflected spectra R(f)=S(f)X(f), and the final processed signal is thus the interference pattern X(f) from the film-Si wafer acoustic interferometer. The film thickness resolution obtainable from X(f) is set by the transducer's bandwidth and acoustic propagation velocity of the film. The time determination therefore can be extrapolated by a Fourier transform.

Figure 6:
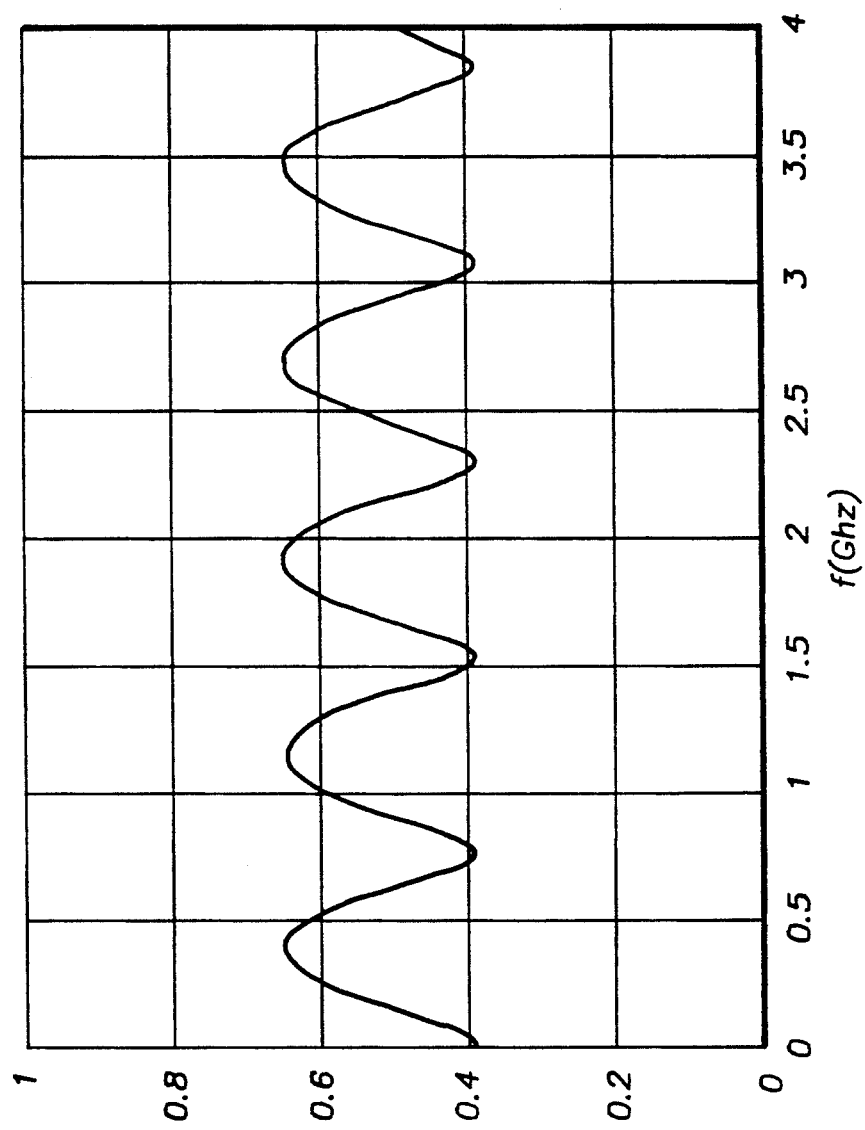
FIG. 6 graphically shows a theoretical plot of reflection coefficient amplitude vs. frequency.

The short acoustic pulse in the time domain can also be viewed as broadband excitation in the frequency domain. A theoretical plot of the frequency domain interference pattern for a 2.1 $\mu$m gold film is shown in FIG. 6. The frequency is represented on the abscissa and the reflection coefficient amplitude is represented on the ordinate.

Figure 7:
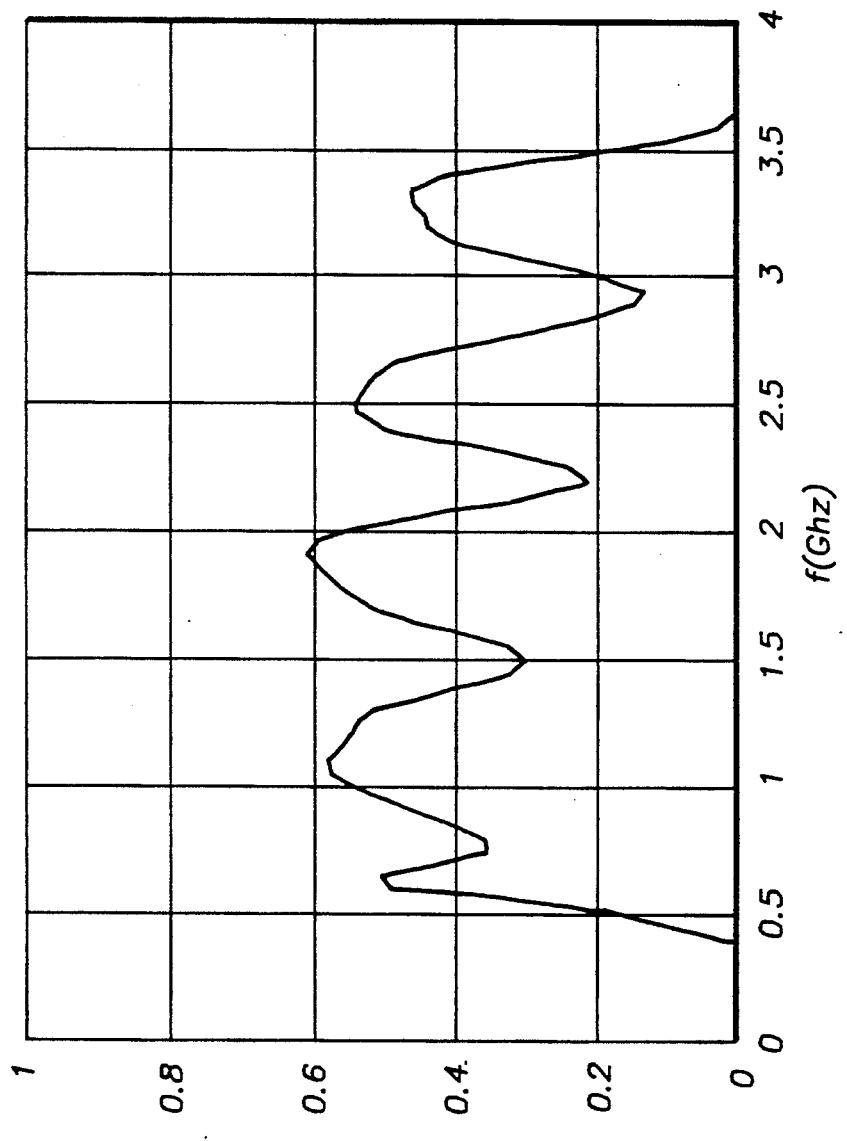
FIG. 7 graphically shows an experimental plot of reflection coefficient amplitude vs. frequency.

An experimental frequency domain interference pattern is shown in FIG. 7. Such a representation can be used to determine the film thickness X by measuring the frequency spacings $\Delta f$ between maximum (or minimum) and using the relation $X = V_0/2\Delta f$. In the example shown in FIG. 7, the average $\Delta f$ was 750 MHz, which corresponds to a film thickness of 2.16 $\mu$m gold film. In the alternative, such a representation can be fitted to predetermined data, for example, like that shown in FIG. 6 for comparison to determine the film thickness X.

In both the time and frequency domains, accurate knowledge of the acoustic velocity $V_0$ is essential for an accurate film thickness measurement. Furthermore, the thickness of both silicon and any film are temperature dependent and therefore, the temperature of the composite unit at the time of sampling must also be taken into account by the relation, for example, $\Delta t = 2L/V$.

Figure 8:
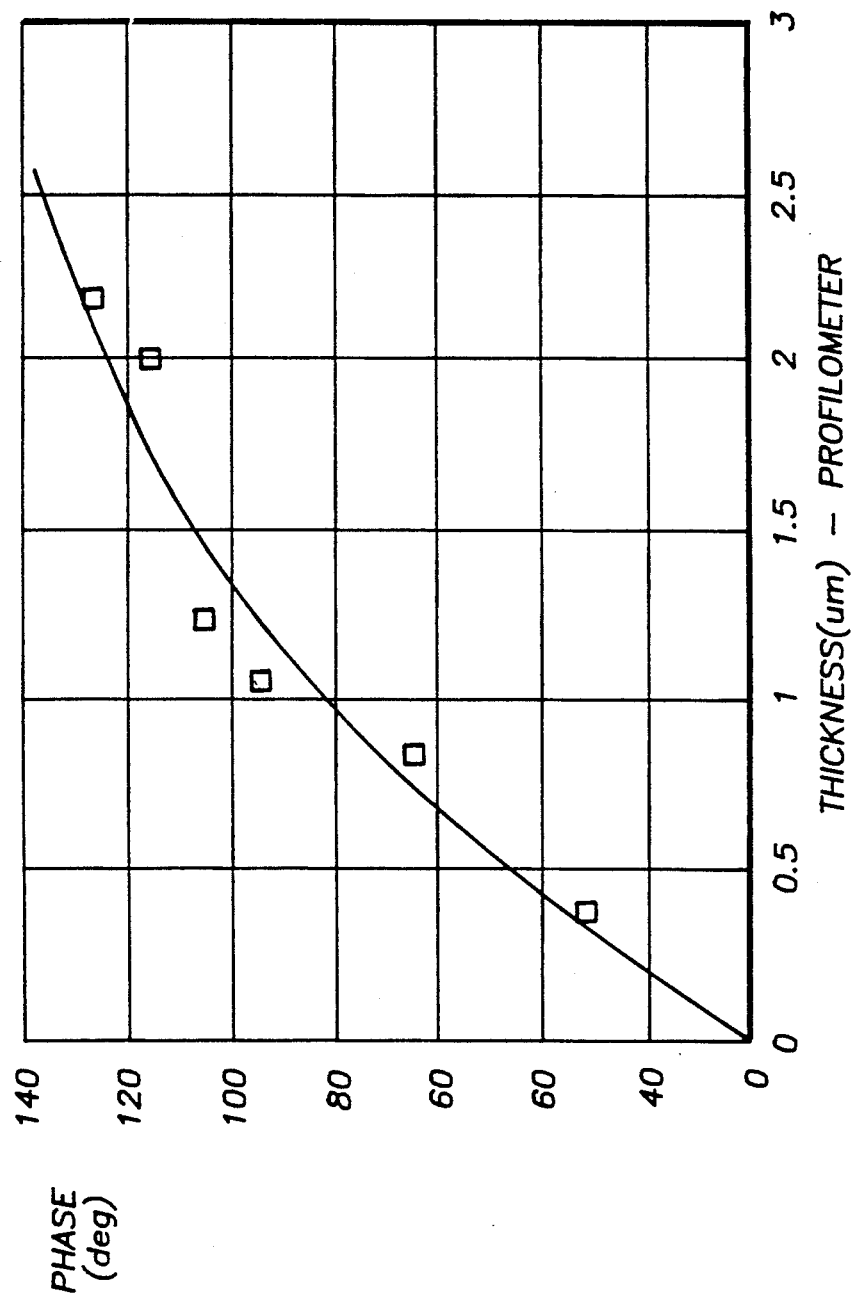
FIG. 8 graphically shows a theoretical plot and experimental data of phase angle vs. film thickness for a gold film.
Figure 9:
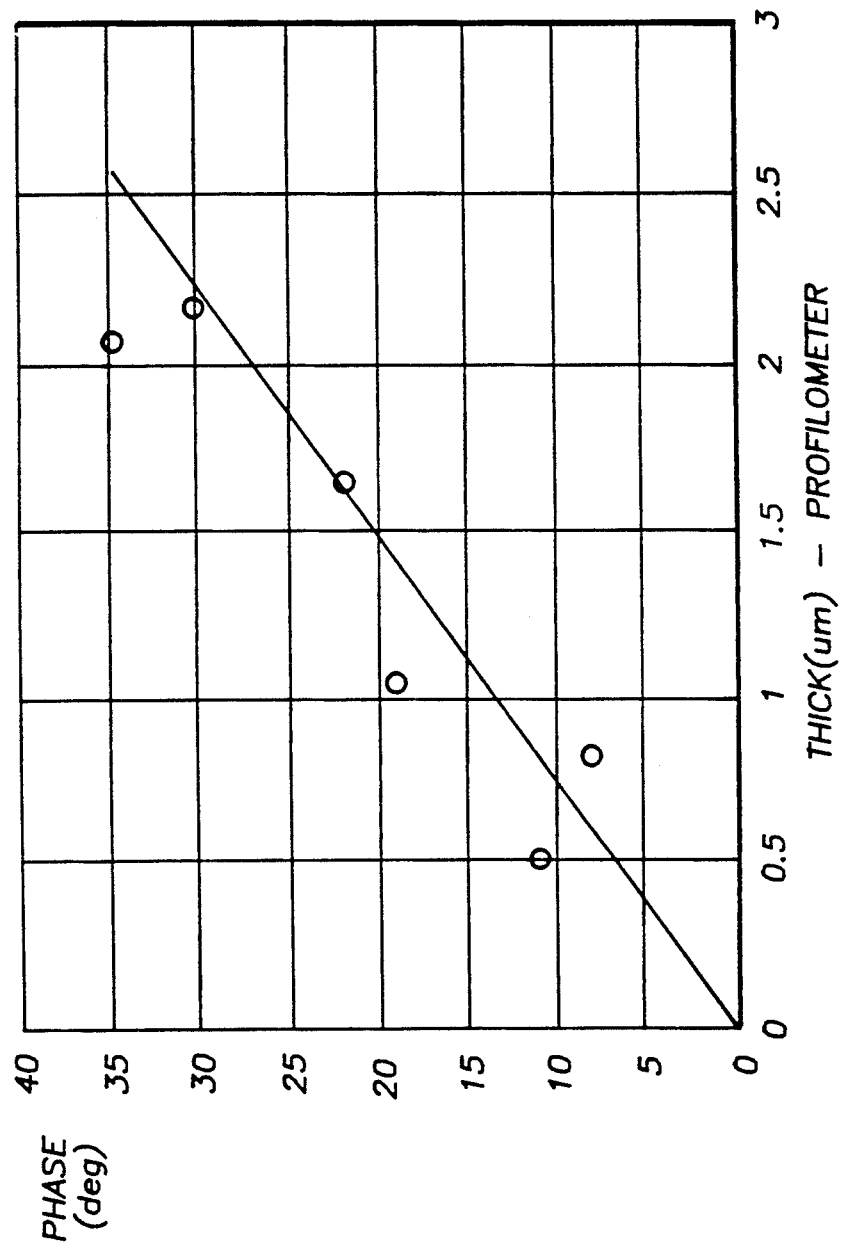
FIG. 9 graphically shows a theoretical plot and experimental data of phase angle vs. film thickness for an aluminum film.

FIG. 8 shows a theoretical plot and experimental data of phase angle vs. film thickness for gold film. FIG. 9 shows a theoretical plot and experimental data of phase angle vs. film thickness for aluminum film. The data for these graphs was collected with a system having a 20 $\mu$m thick LiNbO$_3$ transducer on a quartz buffer rod operated at 135 MHz. Since phase measurements are always relative, two measurements are made on each wafer, one with a bare substrate and one with the film on the substrate. The difference in the two measurements is calculated to obtain a final value of the phase for the metal film. The value of the phase is then compared to theoretical values as shown in FIGS. 8 and 9 to determine the thickness of the film.

The configurations described herein can be used in an in-situ environment or a post processing environment where contact between the buffer rod and the composite unit can be made directly. In the system described, measurements can be made without using a water couplant or any other type of contaminant that would necessitate cleaning before further processing.

Mounting the wafer to the TDR system for in-situ measurements may be done by using an electrostatic chuck which holds the composite unit in place during the measurements or other means suitable for positioning the buffer rod in contact with the composite unit.

In view of the foregoing, it is clear that all of the objectives of the present invention have been met. The general object of the present invention to provide a system and method for non-invasive, in-situ and real time film thickness measurements has been met. Moreover, the object of using the propagation of an acoustic wave through the film and its reflection at a boundary to provide data for determining film thickness. Furthermore, the object of using determinations of time domain, frequency domain and the difference in the phase of the reflected wave with respect to the propagated wave for calculating the film thickness has been met. Finally, the object of generating the acoustic wave with an ultrasonic transducer or a pulse laser has also been met.

While the invention has been shown and described in what is presently conceived to be the most practical and preferred embodiment of the invention, it will become apparent to those skilled in the art that many modifications thereof may be made within the scope of the invention, which scope is to be accorded the broadest interpretation of the claims so as to encompass all equivalent structures and devices.

We claim:

1. A system for measuring thickness of at least one film on a substrate, such constituting a composite unit, said film and substrate having an interface, said system comprising:
    means including a buffer rod having an end shaped to make Hertzian contact with said composite unit for propagating a high frequency acoustic wave through said composite unit, said acoustic wave generating reflected echo waves at the interfaces between the buffer rod and composite, between the composite and air, and between the film and substrate;
    means for receiving said echo waves and generating output signals; and
    means for processing said output signals to give a film thickness value.

2. A system as recited in claim 1 wherein said means for propagating an acoustic wave through said composite unit makes Hertzian contact with the film side of the composite unit.

3. A system as recited in claim 1 wherein said means for propagating acoustic wave through said composite unit makes Hertzian contact with the substrate side of the composite unit.

4. A system as recited in claim 1 wherein said means for processing said output signals comprises:
    means for determining the time separation between said echo waves; and
    means for converting said time separation into thickness data.

5. A system as recited in claim 1 wherein said means for processing said output signals comprises:
    means for determining the frequency domain of said output signals; and
    means for converting said frequency domain signals into thickness data.

6. A system as recited in claim 1 wherein said system further comprises predetermined phase measurement data and wherein said means for processing said output signals comprises:
    means for determining the phase of said echo waves with respect to said propagated wave; and
    means for converting said determined phase into thickness data.

7. A system as recited in claim 1 wherein said propagated wave is generated by an ultrasonic transducer.

8. A system as recited in claim 1 wherein said propagated wave is generated by a pulse laser.

9. An apparatus for measuring the thickness of at least one film on a substrate, such constituting a composite unit, said film and substrate having an interface, said apparatus comprising:
    a buffer rod having one end shaped to make a Hertzian contact with said composite unit;
    a transmitting transducer in communication with the other end of said buffer rod for propagating an acoustic wave through said composite unit, said propagating acoustic wave reflecting off the interface between said buffer rod and composite unit and off of said interface between said film and said substrate to generate echo waves;
    a receiving transducer for receiving said echo waves;
    means for receiving said echo waves and generating an output signal representative between the time lapse between said echo waves; and
    means for processing said output signal to give a thickness value.

10. A method for measuring the thickness of at least one film on a substrate, such constituting a composite unit, said film and substrate having an interface, said method comprising the steps of:
    propagating a high frequency acoustic wave into and through said composite unit by a Hertzian contact, said acoustic wave reflecting off the Hertzian contact-composite unit interface, said interface between said film and said substrate, and the interface between the composite unit and air to generate echo waves;
    receiving said echo waves and generating output signals; and
    processing said output signals to give a film thickness value.

11. A method as recited in claim 10 wherein the step of propagating an acoustic wave propagates the wave first through the film of the composite unit.

12. A method as recited in claim 10 wherein the step of propagating an acoustic wave propagates the wave first through the substrate of the composite unit.

13. A method as recited in claim 10 wherein the step of processing said output signals comprises the steps of:
    determining the time lapse between said echo waves; and converting said time lapse into distance data.

14. A method as recited in claim 10 wherein the step of processing said output signals comprises the steps of:
   determining the frequency domain of said output signals; and
   converting said frequency domain of said signals into thickness data.

15. A method as recited in claim 10 wherein the step of processing said output signals comprises the steps of:
   determining the phase of the reflection coefficient of said echo waves with respect to said propagated wave; and
   converting said determined phase into thickness data.

16. A method as recited in claim 10 wherein said acoustic wave is generated by an ultrasonic transducer.

17. A method as recited in claim 10 wherein said acoustic wave is generated by a pulse laser.

* * * * *